United States Patent [19]

Pickart

[11] Patent Number: 5,348,943
[45] Date of Patent: * Sep. 20, 1994

[54] COSMETIC AND SKIN TREATMENT COMPOSITIONS

[75] Inventor: Loren R. Pickart, Bellevue, Wash.

[73] Assignee: ProCyte Corporation, Redmond, Wash.

[*] Notice: The portion of the term of this patent subsequent to May 12, 2004 has been disclaimed.

[21] Appl. No.: 924,324

[22] Filed: Aug. 3, 1992

Related U.S. Application Data

[60] Division of Ser. No. 207,698, Jun. 16, 1988, Pat. No. 5,135,913, which is a continuation-in-part of Ser. No. 48,444, May 11, 1987, abandoned, which is a continuation-in-part of Ser. No. 699,824, Feb. 8, 1985, Pat. No. 4,665,054.

[51] Int. Cl.$^5$ .................. A61K 37/02; C07K 5/08; C07K 5/10; C07K 7/06
[52] U.S. Cl. ........................ 514/18; 514/16; 514/17; 530/331
[58] Field of Search .............. 514/17, 18, 16; 530/331

[56] References Cited

U.S. PATENT DOCUMENTS

| | | | |
|---|---|---|---|
| 3,194,732 | 7/1965 | Nauhauser | 514/16 |
| 3,551,554 | 12/1970 | Herschler | 424/7 |
| 3,558,770 | 1/1971 | Gordon et al. | 514/884 |
| 3,758,682 | 9/1973 | Huber et al. | 514/16 |
| 3,767,784 | 10/1973 | Gluck | 514/21 |
| 3,832,338 | 8/1974 | Huber et al. | 514/21 |
| 4,022,888 | 5/1977 | Huber et al. | 514/21 |
| 4,167,945 | 9/1979 | Gottlieb | 514/560 |
| 4,177,261 | 12/1979 | Dietze et al. | 514/16 |
| 4,263,428 | 4/1981 | Apple et al. | 536/17 |
| 4,287,184 | 9/1981 | Young | 514/21 |
| 4,440,788 | 4/1984 | Terayama et al. | 514/562 |
| 4,665,054 | 5/1987 | Pickart | 514/18 |
| 5,135,913 | 8/1992 | Pickart | 514/16 |

OTHER PUBLICATIONS

Kwa, Ph.D. Thesis, University of Washington, 1983.
Pickart et al., J. Cell. Physiol. 102(2): 129-139, 1980, Cited in Chem. Abs. 93: 1155m, 1980).
Williams et al., Cytobios, 27(105):19-25, 1980, (Cited in Chem. Abstracts vol. 94: 25451b, 1981).
Mochida Pharmaceutical Co. Ltd., "Antinflammatory Injections Containing Superoxide Dismutase," Jpn. Kokai Tokkyo Koho, 81: 07720, 1981 (Cited in Chem. Abstracts, vol. 94: 145386f, 1981).
Loker, Ph.D. Thesis, University of Washington, 1980.
Pickart, Lymphonkines 8: 425-446, 1983.
Poole et al., Cancer Research 43: 5857-5861, 1983.
Raju et al., JNCI 69(5): 1183-1188, 1982.
Freedman et al., Biochemistry 21: 4540-4544, 1982.
Kwa et al., Peptides: Structure and Function 8: 805-808, 1983.
Perkins et al., Inorganic Chimica Acta 82: 93-99, 1984.
Kimoto et al., Cancer Research 43: 824-828, 1963.
Sorenson, Comprehensive Therapy 11(4): 49-64 1985.
Pickart et al., Biochem. Pharmacol. 32(24): 3868-3871, 1983.
Pickart et al., Nature 288: 715-717, 1980.
Natural Healing Annual 1986, p. 38 (Edit M. Bricklin, Prevention Magazine, Rodale Press, Emmaus, Pa.).
Pickart et al., Biochem. Res. Commun. 54(2): 526-536, 1973.

*Primary Examiner*—Lester L. Lee
*Attorney, Agent, or Firm*—Seed and Berry

[57] ABSTRACT

Methods and compositions for (a) improving and/or maintaining the health of skin, and (b) increasing subcutaneous fat in warm-blooded animals are disclosed. The methods utilize an effective amount of a composition comprising GHL—Cu or a derivative of GHL—Cu.

6 Claims, 3 Drawing Sheets

COSMETIC AND SKIN TREATMENT COMPOSITIONS

CROSS-REFERENCE TO RELATED APPLICATIONS

This application is a divisional of U.S. Ser. No. 07/207,698, filed Jun. 16, 1988 now U.S. Pat. No. 5,135,913; which is a continuation-in-part of U.S. Ser. No. 07/048,444, filed May 11, 1987 now abandoned; which is a continuation-in-part of U.S. Ser. No. 06/699,824, filed Feb. 8, 1985, which issued as U.S. Pat. No. 4,665,054 on May 12, 1987.

TECHNICAL FIELD

The present invention relates to cosmetic compositions in general, and more specifically, to the use of derivatives of glycyl-L-histidyl-L-lysine: copper(II) (GHL—Cu) within skin treatment and cosmetic compositions.

BACKGROUND OF THE INVENTION

Skin problems in individuals can result from a variety of causes: environmental assault (e.g., sun and wind), internal disease (e.g., diabetes, atherosclerosis) or normal aging. A number of structural and functional skin changes occur with aging. Further, because of the interrelationship between the structure and function of the skin, structural changes resulting from the aging process may also lead to concomitant functional impairment.

Age-associated changes are readily apparent in the epidermis, where there is an increased propensity for blistering and/or erosion. Microscopically, it has been observed that the epidermal basal cells of aged skin display greater variability in their size, shape and staining qualities than those obtained from more youthful skin. In addition, the moisture content of the stratum corneum is decreased, and cellular cohesion is diminished, particularly at the periphery of the corneocytes.

Clinically, the problem of rough or dry skin is a manifestation of several morphological changes, including the decreased moisture content of the stratum corneum, coupled with reduced eccrine and sebaceous gland output. As a person ages, there is a decrease in the epidermal turnover time, especially after the age of 50. Clinically, superficial wounds take more time to heal, making the elderly more prone to secondary infection following minor trauma.

As the skin ages, the dermis decreases in density and becomes relatively acellular and avascular. Throughout adult life, the total amount of collagen decreases about one percent per year. The collagen fibers thicken, becoming less soluble, have less capacity for swelling, and become more resistant to digestion by collagenase. There are also structural aberrations in the elastic fibers of the reticular dermis that contribute to skin sagging and a predisposition to injury.

The regression of the subepidermal elastic network may contribute to cutaneous laxity and the subtle wrinkled appearance prevalent on sun-protected skin of the elderly. Atrophy of the dermis and subcutaneous fat also plays an important role in the formation of wrinkles.

In addition, the dermis of elderly individuals has approximately 50% fewer mast cells than does that of a younger person. Clinically, this has cosmetic as well as physiologic implications. Cosmetically, the skin becomes pale with advancing age. Physiologically, the elderly patient is predisposed to both hyperthermia and hypothermia, following seemingly insignificant changes in ambient temperature. Basically, a smaller volume of blood can be diverted to the reduced capillary network of the papillary dermis following elevations in the body's core temperature, thereby diminishing cooling and resulting in hyperthermia.

Conversely, hypothermia results from the body's inability to efficiently divert blood from the skin to help conserve body heat when ambient temperatures decrease. This problem is compounded by the loss of insulating subcutaneous tissue that generally occurs in the elderly.

Many preparations have been developed for the purpose of treating human skin in an effort to counter the structural changes briefly described above, or merely to temporarily enhance the appearance of the skin. Many such preparations are directed toward moisturizing, thereby protecting the skin against drying. In general, numerous cosmetic preparations intended to combat aging in the skin exist on the market, and these preparations contain a wide variety of compounds, such as biological extracts, for example placental extracts, collagen, polyvitamin mixtures, and essential fatty acids.

However, due to the general ineffectiveness of these compositions, there exists a need in the art for improved compositions for making skin healthier, from both a structural and appearance standpoint. The present invention fulfills this need, while further providing other related advantages.

DISCLOSURE OF THE INVENTION

Briefly stated, the present invention discloses skin treatment and cosmetic compositions useful for maintaining and improving the health of skin. The compositions of the present invention generally comprise an effective amount of GHL—Cu, or a derivative of GHL—Cu having the general formula:

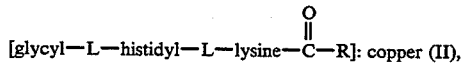

wherein R is selected from the group consisting of alkyl moieties containing from one to eighteen carbon atoms, aryl moieties containing from six to twelve carbon atoms, alkoxy moieties containing from one to twelve carbon atoms, and aryloxy moieties containing from six to twelve carbon atoms, or where R is L-prolyl-L-valyl-L-phenylalanyl-L-valine or L-valyl-L-phenylalanyl-L-valine. Within a preferred embodiment, the alkyl moiety is an unbranched chain, such as an N-octyl moiety. Further, the alkyl moiety may be an N-stearyl moiety or an N-palmityl moiety.

The compositions of the present invention, by virtue of their skin health promoting characteristics, also have a marked cosmetic effect, leaving the skin with a soft, pleasing, fresh appearance.

Within one aspect of the present invention, a method for increasing subcutaneous fat in warm-blooded animals is disclosed. The method comprises administering to the animal an effective amount of a composition comprising a derivative of GHL—Cu having the general formula:

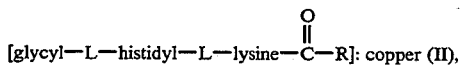

[glycyl—L—histidyl—L—lysine—C(=O)—R]: copper (II), wherein R is selected from the group consisting of alkyl moieties containing from one to eighteen carbon atoms, aryl moieties containing from six to twelve carbon atoms, alkoxy moieties containing from one to twelve carbon atoms, and aryloxy moieties containing from six to twelve carbon atoms, or where R is L-prolyl-L-valyl-L-phenylalanyl-L-valine or L-valyl-L-phenylalanyl-L-valine.

Within another aspect of the present invention, a method for improving and/or maintaining the health of skin is disclosed. The method generally comprises administering to the skin an effective amount of a composition comprising GHL—Cu or a derivative of GHL—Cu having the general formula:

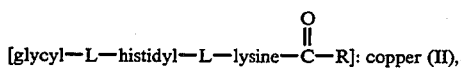

[glycyl—L—histidyl—L—lysine—C(=O)—R]: copper (II), wherein R is selected from the group consisting of alkyl moieties containing from one to eighteen carbon atoms, aryl moieties containing from six to twelve carbon atoms, alkoxy moieties containing from one to twelve carbon atoms, and aryloxy moieties containing from six to twelve carbon atoms, or where R is L-prolyl-L-valyl-L-phenylalanyl-L-valine or L-valyl-L-phenylalanyl-L-valine.

In addition to the derivatives described above, other chemical modifications may be made to alter the biological activity of the derivatives of the present invention. For instance, glycine may be replaced by a variety of other small amino acids, including alanine, serine and valine. Further, the copper(II) binding affinity of the molecule could be increased by addition of an N-terminal amino acid such as glycine to convert glycyl-L-histidyl-L-lysine to glycyl-L-glycyl-L-histidyl-L-lysine. In addition, glycine could be added to a derivative as described above to create the corresponding tetrapeptide.

The compositions described herein may be injected intradermally or applied topically, and are rendered suitable for administration to warm-blooded animals for the purposes of the present invention by combining the derivative with a vehicle which adapts the composition for either intradermal injection or topical application. Suitable topical formulations may be prepared with common cosmetic, nontoxic, nonallergenic carriers for use in skin creams, lotions, sprays, liquids, emollients, cleansing preparations and the like.

Other aspects of the present invention will become evident upon reference to the following detailed description and attached drawings.

BEST MODE FOR CARRYING OUT THE INVENTION

Figure 1:
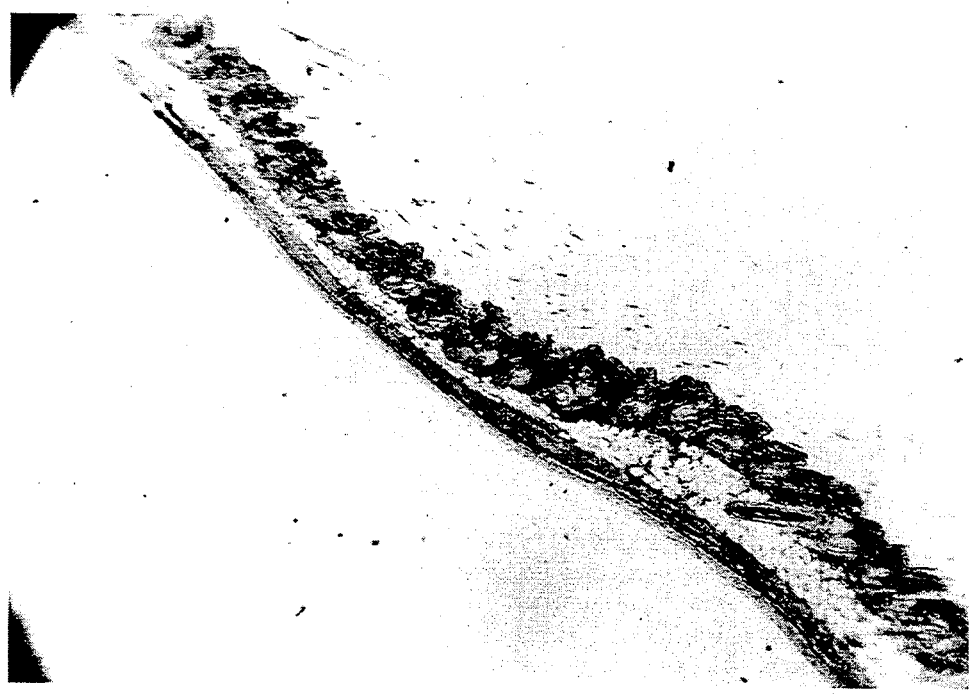
FIG. 1 is a microphotograph of a biopsy section illustrating the formation of a heavy field of large, subcutaneous fat cells, as shown toward the right side of the figure.

As briefly noted above, skin characteristics change as humans age, and the skin's ability to both resist insults and restore itself diminishes. Skin loses its suppleness and softness, becomes thinner due to less collagen and subcutaneous fat in the skin, attains a rougher surface, is often populated by areas of damaged skin ("aging spots"), and is more wrinkled. The following table illustrates the histologic features of aging human skin:

TABLE

| HISTOLOGIC FEATURES OF AGING HUMAN SKIN | | |
| --- | --- | --- |
| Epidermis | Dermis | Appendages |
| Flattened dermo-epidermal junction | Atrophy (loss of dermal volume) | Depigmented hair Loss of Hair |
| Variable thickness | Fewer fibroblasts | Conversion of terminal to vellus hair |
| Variable cell size and shape | Fewer mast cells Fewer blood vessels | |
| Occasional nuclear atypia | Abnormal nerve endings | Abnormal nail-plates |
| Fewer Langerhans cells | | Fewer glands |

As described herein, GHL—Cu and various derivatives of GHL—Cu may be used to improve the health of skin in individuals and other warm-blooded animals. In addition, these derivatives can be tailored to increase their fat solubility, resulting in a form of the molecule which is more useful in a formulation of pharmaceutical and cosmetic creams and gels.

The compositions of the present invention function to improve skin health by acting as potent in vivo chemoattractants for cells important in the maintenance of skin defenses and health such as macrophages, monocytes and mast cells. These white cells both protect the skin from invading organisms and secrete growth factors, such as epidermal growth factor, fibroblast growth factor, platelet-derived growth factor and transforming growth factor, that function in the maintenance of healthy skin cells.

The compositions of the present invention are also angiogenic and can induce new capillary growth into elderly skin that lacks sufficient blood flow. Much of the attractive appearance of the skin of young children is due to the heavy blood flow through capillaries near the skin surface. This imparts a reddish component to the skin color which increases attractiveness to the skin. As humans age, this reddish component is reduced, giving a more colorless skin.

The compositions of the present invention also have significant superoxide dismutase-like activity, a property linked with anti-inflammatory effects which act by detoxifying skin-damaging oxygen radicals. (U.S. Pat. No. 4,595,456)

The compositions of the present invention also stimulate the production of the major skin protein, collagen, by fibroblasts. Much of the wrinkling in older skin is due to a reduction in the collagen content of the skin.

The derivatives of the present invention are described in detail in U.S. Pat. No. 4,877,770 and U.S. Pat. No. 4,665,054, which documents are hereby incorporated by reference. The derivatives of the present invention may be prepared by esterification, by the removal of a water molecule, or by the addition of a group (either an alcohol such as octanol, methanol, benzol alcohol or $NH_3$)

to the carboxylic acid terminus of GHL, resulting in the formation of the more lipophilic derivative. This increases fat solubility by (1) removal of the electric charge associated with the carboxylic acid group and (2) the introduction of hydrophilic groups into the molecule.

The overall chemical reaction in this transformation may be characterized as:

$$GHL-OH + R-H \rightarrow GHL-R + H_2O.$$

In practice, the reaction is most readily carried out by adding the R group to the amino acid lysine prior to the combination of lysine with the other two amino acids to GHL. After the formation and isolation of GHL—R, the copper(II) is chelated to the molecule to form the bioactive complex.

The overall reaction to form the more lipophilic derivatives of GHL—Cu may be characterized:
1) lysine-OH + R—H → lysine-R + $H_2O$
2) lysine-R + blocked L-histidine → blocked L-histidine-L-lysine-R
3) blocked L-histidine-L-lysine-R + blocked-glycine → blocked glycyl-L-histidine-L-lysine-R
4) blocked glycyl-L-histidine-L-lysine-R → glycyl-L-histidine-L-lysine-R
5) glycyl-L-histidine-L-lysine-R + copper(II) → glycyl-L-histidine-L-lysine-R: copper(II).

Within preferred embodiments, the derivative of GHL and copper are present in a 1:1 or 2:1 ratio.

The derivatives of the present invention have clinical use in at least three primary areas: (1) improving and/or maintaining the health of skin, (2) increasing the subcutaneous fat content, and (3) in general cosmetic applications. These cosmetic applications include: (a) improving skin softness and suppleness, (b) increasing skin depth and reducing wrinkles, (c) reducing aging spots, (d) reducing skin nodules and pimples, and (e) clearing microhemorrhages and petechiae from the skin surface.

Within the present invention, it is generally preferred to administer the derivatives described herein intradermally or topically in the center of the area to be treated, along with a suitable vehicle in a concentration of approximately 50 micrograms of derivative per 0.1 ml of vehicle. It is preferable to use a dosage of approximately 9 micrograms per cm² of area to be treated, although dosages greater than 9 micrograms/cm² up to approximately 40 micrograms/cm², may be used. Suitable vehicles in this regard include saline. When used in the form of a cream or gel and applied topically, it is useful to add a suitable penetrating agent, such as DMSO (U.S. Pat. No. 3,527,864) or eucalyptol (U.S. Pat. No. 4,560,553), to the composition. Suitable vehicles for use in cosmetic applications will be evident to those skilled in the art.

For topical application, the compositions of the present invention may be in the form of a cream, gel, milk, lotion or oil for the skin. Further, the compositions may be coupled with suitable excipients adapted for application to the face and the neck. Appropriate excipients should have a high affinity for the skin, be well tolerated, stable, and present an adequate consistency enabling easy and pleasant utilization. Examples of excipients in this regard include a mixture of isopropyl myristate, glycerol sterate, sweet almond oil and polyhydric alcohol (respectively 5 grams (g)—15 g—6 g—5 g for 100 ml of distilled water).

Additional ingredients may be added according to the understanding of those familiar with the art in order to vary the texture, consistency, viscosity, and appearance of the formulation. These additional ingredients include emulsifying agents such as non-ionic ethoxylated and nonethoxylated surfactants, fatty alcohols, fatty acids, organic or inorganic bases, preserving agents, wax esters, steroid alcohols, triglyceride esters, phospholipids such as lecithin and cephalin, polyhydric alcohol esters, fatty alcohol ethers, hydrophilic lanolin derivatives, hydrophilic beeswax derivatives, hydrocarbon oils such as palm oil, coconut oil, mineral oil, cocoa butter waxes, silicon oils, pH balancers and cellulose derivatives.

The compositions of the present invention may also contain small quantities of solar radiation filters or sunscreens, for example, UV-A and UV-B radiation filters, such as hydroxy 2-methoxy 4-benzophene, and dimethoxy 3,4-phenyl glyoxylic acid in the form of its sodium salt. The compositions may further contain humectants favoring the hydration of the skin such as urea, pyrrolidone carboxilic acid and its salts, vitamin extracts, perfumes, preservatives and colors.

To summarize the examples which follow, Example I illustrates the synthesis of glycyl-L-histidyl-L-lysine benzyl ester: copper(II). Example II demonstrates the synthesis of glycyl-L-histidyl-L-lysine n-octyl ester: copper(II). Example III illustrates (A) the synthesis of glycyl-L-histidyl-L-lysine n-stearyl ester: copper(II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-palmityl ester: copper (II). Example IV illustrates the synthesis of glycyl-L-histidyl-L-lysyl-L-prolyl-L-valyl-L-phenylalanyl-L-valine: copper (II) and glycyl-L-histidyl-L-lysyl-L-valyl-L-phenylalanyl-L-valine: copper-(II). Examples V, VI, and VII demonstrate the use of various derivatives of the present invention to stimulate or increase the formation of the subcutaneous fat layer. Example VIII demonstrates the use of a representative composition of the present invention in clearing microhemorrhages from the skin surface. Example IX demonstrates the use of a representative composition of the present invention in reducing skin nodules. Example X demonstrates the use of a representative composition of the present invention in reducing the depth of wrinkles. Example XI demonstrates the use of a representative composition of the present invention in treating skin characterized by an eczema-like surface. Example XII demonstrates the use of representative composition of the present invention in reducing aging spots. Example XIII demonstrates the use of a representative composition of the present invention in the treatment of pimples.

The following examples are offered by way of illustration and not by way of limitation.

EXAMPLES

Sources of Chemicals

Chemicals and peptide intermediates utilized in the following examples may be purchased from the following suppliers: Sigma Chemical Co. (St. Louis, Mo.); Peninsula Laboratories (San Carlos, Calif.); Aldridge Chemical Co. (Milwaukee, Wis.); Vega Biochemicals (Tucson, Ariz.); Pierce Chemical Co. (Rockford, Ill.); Research Biochemicals (Cleveland, Ohio); Van Waters and Rogers (South San Francisco, Calif.); Bachem, Inc. (Torrance, Calif.).

EXAMPLE I

Synthesis of glycyl-L-histidyl-L-lysine benzyl ester: Copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to benzyloxycarbonylglycine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1 M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine benzyl ester: copper(II).

EXAMPLE II

Synthesis of glycyl-L-histidyl-L-lysine n-octyl ester: copper (II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper-complex by the addition of an equimolar quantity of copper diacetate. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine n-octyl ester: copper(II).

EXAMPLE III

A. Synthesis of glycyl-L-histidyl-L-lysine n-stearyl ester: copper (II)

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl $N^e$-benzyloxycarbonyl-L-lysinate. The product was dissolved in tetrahydrofuran and mixed with $N^a$-t-butyloxycarbonyl-$N^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^e$-benzyloxycarbonyl-L-lysinate, which was dissolved tetrahydrofuran, isobutyl chloroformate, N-methylmorpholine and benzyloxycarbonylglycine to form n-stearyl benzyloxycarbonylglycyl-$N^{im}$-benzyloxycarbonyl-L-histidyl-$N^e$-benzyloxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester: copper(II)

N(ε)-benzyloxycarbonyl-L-lysine, n-stearyl alcohol, p-toluenesulfonic acid monohydrate, and benzene are refluxed together using a Dean-Stark trap to azeotropically remove the evolved water. After cooling to room temperature and then adding dry ethyl ether, n-stearyl N(ε)-benzyloxycarbonyl-L-lysinate p-toluenesulfonate salt is collected by filtration, treated with 2 M aqueous potassium bicarbonate solution, and extracted into dichloromethane. Evaporation gives the free amine, which is redissolved in dry tetrahydrofuran (THF) and added to a stirring solution of N(α)-t-butyloxycarbonyl-N(im)-benzyloxycarbonyl-L-histidine, N-methylmorpholine, and isobutyl chloroformate in dry THF at −15° C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

EXAMPLE IV

Synthesis of glycyl-L-histidyl-L-lysyl-L-prolyl-L-valyl-L-phenylalanyl-L-valine: copper(II) and of glycyl-L-histidyl-L-lysyl-L-valyl-L-phenylalanyl-L-valine: copper(II)

These peptides are synthesized by standard solid-phase methods common to the peptide field (J. Stewart and J. Young, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

EXAMPLE V

Use of Glycyl-L-Histidyl-L-Lysine N-octyl Ester: Copper(II) to Increase the Formation of the Subcutaneous Fat Layer A single dose of 50 micrograms of glycyl-L-histidyl-L-lysine n-octyl ester: Cu(II) was infiltrated under the skin in eight mice. Increased amounts of subcutaneous fat were observed.

In another series of experiments, mice were injected once with glycyl-L-histidyl-L-lysine octyl ester:Copper(II) at a dose of 500 micrograms per mouse.

In the region of administration, there was a significant increase in the thickness of the subcutaneous fat layer. This increase in subcutaneous fat is shown by taking a biopsy sample at day 21 through the area and sectioning for histology slides. FIG. 1 shows this increase in the fat layer. The injected area is on the right with the adjacent uninjected area on the left of the photograph. There was an increase in both the number and size of the fat cells. Measurements demonstrate that there was an approximately three-fold increase in the subcutaneous fat layer in the skin near the injection site.

EXAMPLE VI

Figure 2:
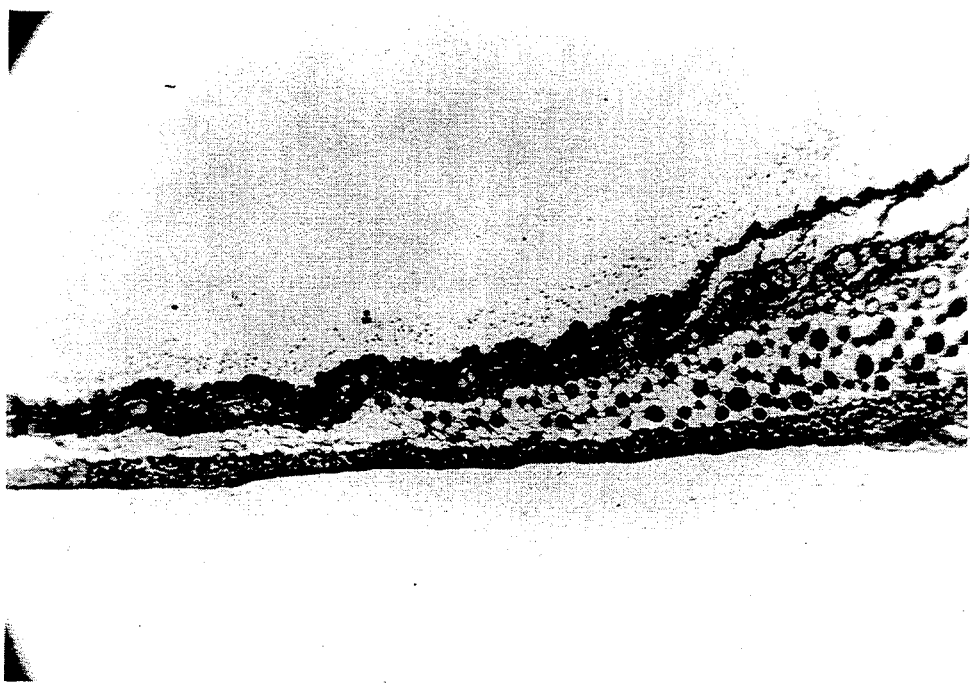
FIG. 2 is a microphotograph of a biopsy section illustrating the formation of a subcutaneous fat cell layer in the area near the injection site.

Use of glycyl-L-histidyl-L-lysine Decyl ester Copper(II) to Stimulate Formation of the Subcutaneous Fat Layer A group of ten mice were injected once with glycyl-L-histidyl-L-lysine decyl ester: Copper(II) at a dose of 500 micrograms per mouse. Microscopic examination provided evidence of increased fat cell layer in the area surrounding the injection site. FIG. 2 shows this marked increase in the subcutaneous fat layer at the area of injection. Examination of the skin distant from the injection site showed a normal histology.

EXAMPLE VII

Figure 3:
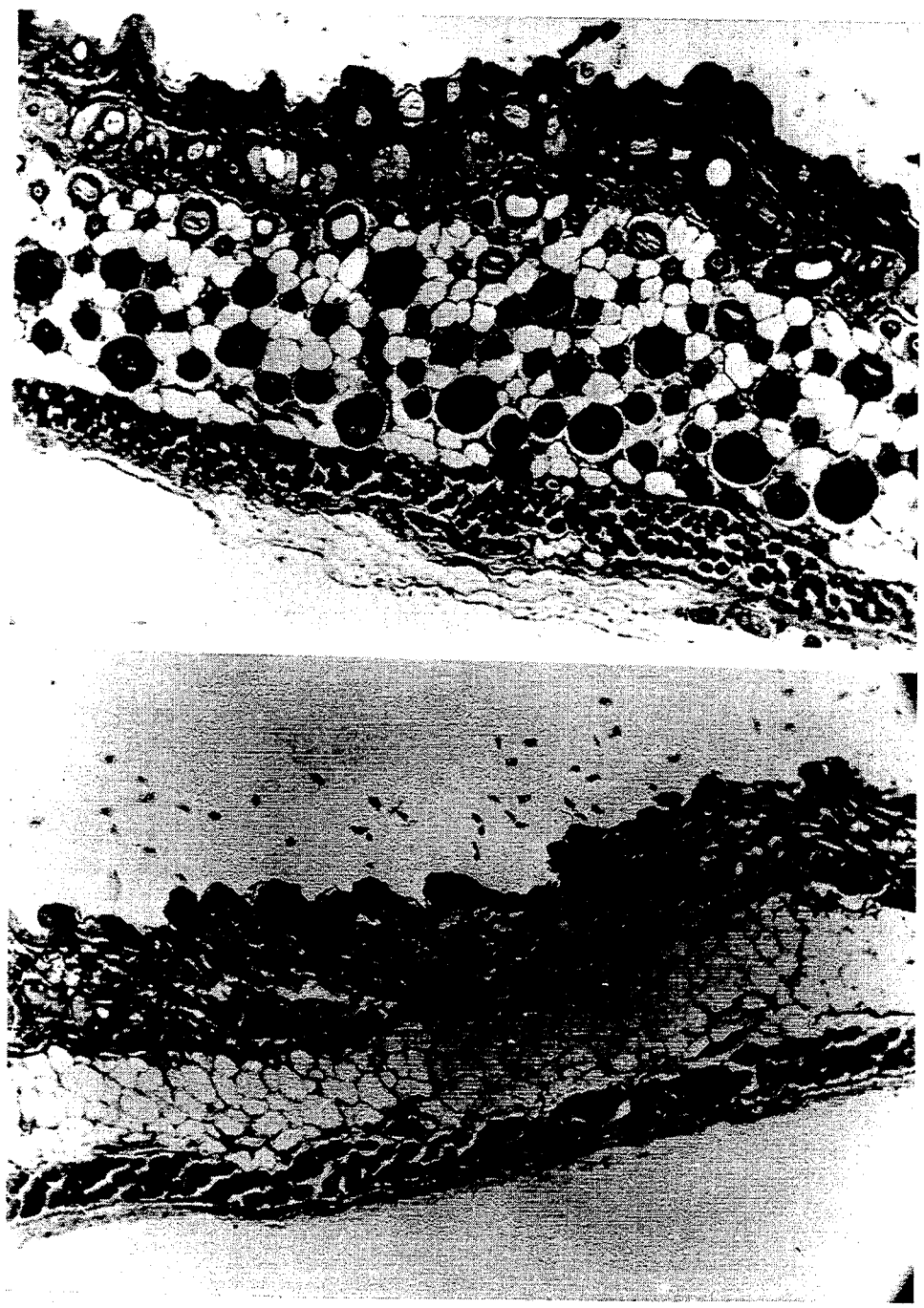
FIG. 3 is a microphotograph of a control area (bottom) and an area of increased subcutaneous fat cells (top) generated through use of a representative derivative of the present invention.

Use of glycyl-L-histidyl-L-lysine Palmityl ester Copper(II) to Increase the Formation of the Subcutaneous Fat Layer A group of ten mice were injected once with glycyl-L-histidyl-L-lysine palmityl ester: Copper(II) at a dose of 500 micrograms per mouse. Histological sections through the area of injection were similar to those described in Example VI. FIG. 3 is a photomicrograph demonstrating an increase in the subcutaneous fat layer, similar to that seen following the glycyl-L-histidyl-L-lysine decyl ester: Cu injection.

EXAMPLE VIII

An 82 year old woman had skin covered by a sprinkled pattern of fine reddish spots of microhemorrhages beneath an irritated skin surface. Application, once daily for 9 days, of an ointment (97% Unibase and 3% nonoxynol-9) containing 4 mg GHL—Cu per gram resulted in a complete clearing of the reddish spots and an improved skin appearance.

EXAMPLE IX

A 73 year old woman had a skin surface with numerous small reddish elevated nodules (slightly smaller than pimples). Treatment with the ointment used in Example VIII resulted in a marked reduction in the nodules within 10 days. By 20 days, the skin was completely clear with a smooth, healthy, and attractive appearance.

EXAMPLE X

In a 72 year old woman who had skin covered with heavy wrinkles, application of the cream used in Example VIII for 28 days markedly reduced the depth of wrinkles and gave a smoother skin appearance.

EXAMPLE XI

A 77 year old woman had skin covered with a scaly eczema-like surface. Treatment of the skin for 45 days with the ointment used in Example VIII resulted in a sloughing off of the scaly skin and its replacement by a new and more attractive layer of skin.

EXAMPLE XII

A 48 year old man with hair loss and numerous pigmented spots ("aging spots") was treated for 14 days on the top of his head with an ointment (consisting of 94% Unibase and 6% dimethysulfoxide) containing 4 milligrams of GHL—Cu octyl per gram. Thirty days after the start of the treatment there was a marked reduction in the number of aging spots and a reduction in the size of the remaining spots. The skin covering the head became noticeably softer to the touch and possessed a greater thickness.

EXAMPLE XIII

A 40 year old woman had irritated skin with numerous pimples. Treatment for four days with the ointment used in Example VIII resulted in a clearing of the skin and a reduction in the pimple size. By eight days after the start of the treatment, the pimples were completely resorbed, leaving a clear and attractive skin surface.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A skin treatment composition, comprising GHL—Cu or a derivative of GHL—Cu having the formula:

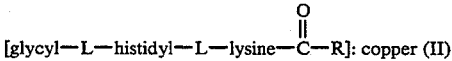

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 18 carbon atoms, or where R is L-prolyl-L-valyl-L-phenylalanyl-L-valine or L-valyl-L-phenylalanyl-L-valine, in combination with a cosmetically and dermatologically acceptable carrier or diluent.

2. The composition of claim 1 wherein the carbon portion of the alkoxy moiety is an unbranched chain.

3. The composition of claim 2 wherein the unbranched chain is an n-octyl moiety.

4. The composition of claim 2 wherein the unbranched chain is an n-stearyl moiety.

5. The composition of claim 2 wherein the unbranched chain is an n-palmityl moiety.

6. The composition of claim 1 wherein the aryloxy moiety is an O-benzyl moiety.

* * * * *

UNITED STATES PATENT AND TRADEMARK OFFICE
CERTIFICATE OF CORRECTION

PATENT NO. : 5,348,943
DATED : September 20, 1994
INVENTOR(S) : Loren R. Pickart It is certified that error appears in the above-identified patent and that said Letters Patent is hereby corrected as shown below:

<u>Title page,</u>
Item [*] Notice, "The portion of the term of this patent subsequent to May 12, 2004 has been disclaimed." should be changed to read -- This patent is subject to a terminal disclaimer. --

Signed and Sealed this

Twenty-seventh Day of April, 2004

JON W. DUDAS
*Acting Director of the United States Patent and Trademark Office*